(12) United States Patent
Pianca

(10) Patent No.: US 9,101,755 B2
(45) Date of Patent: Aug. 11, 2015

(54) SYSTEMS AND METHODS FOR MAKING AND USING CONTACT ASSEMBLIES FOR LEADS OF ELECTRICAL STIMULATION SYSTEMS

(71) Applicant: BOSTON SCIENTIFIC NEUROMODULATION CORPORATION, Valencia, CA (US)

(72) Inventor: Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/098,334

(22) Filed: Dec. 5, 2013

(65) Prior Publication Data
US 2014/0188201 A1 Jul. 3, 2014

Related U.S. Application Data

(60) Provisional application No. 61/746,285, filed on Dec. 27, 2012.

(51) Int. Cl.
*A61N 1/05* (2006.01)
*H01R 24/58* (2011.01)

(52) U.S. Cl.
CPC ............. *A61N 1/05* (2013.01); *A61N 1/0551* (2013.01); *H01R 24/58* (2013.01); *H01R 2201/12* (2013.01); *Y10T 29/49117* (2015.01)

(58) Field of Classification Search
CPC ......... A61N 1/36; A61N 1/08; A61N 1/0472; A61N 1/0476; A61N 1/048; A61N 1/05; A61N 1/0551; Y10T 29/49117
USPC ........................................ 607/115, 116, 148
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,058,454 B1 * | 6/2006 | Chitre et al. ............ 607/116 |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,891,085 B1 | 2/2011 | Kuzma et al. |
| 7,949,395 B2 | 5/2011 | Kuzma |

(Continued)

*Primary Examiner* — Christopher D Koharski
*Assistant Examiner* — Michael Carey
(74) *Attorney, Agent, or Firm* — Lowe Graham Jones PLLC; Bruce E. Black

(57) ABSTRACT

A contact assembly of an electrical stimulation lead includes a body formed from an electrically-nonconductive, molded material. A first end of the body is configured for coupling to an end of an electrical stimulation lead. Side ports are defined along an outer side surface of the body. Each side port is longitudinally offset from the remaining side ports along a longitudinal length of the contact assembly. Conductor lumens are defined along the body. Each of the conductor lumens extends from the first end of the body and terminates with a different one of the side ports such that each of the conductor lumens has a different length than every other of the conductor lumens. A stylet lumen having a closed end is defined along the body. The stylet lumen extends longitudinally from the first end of body and terminates at the closed end.

20 Claims, 11 Drawing Sheets

(56) References Cited

U.S. PATENT DOCUMENTS

| | | |
|---|---|---|
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2005/0090885 A1* | 4/2005 | Harris et al. ............ 607/116 |
| 2007/0150036 A1 | 6/2007 | Anderson |

* cited by examiner

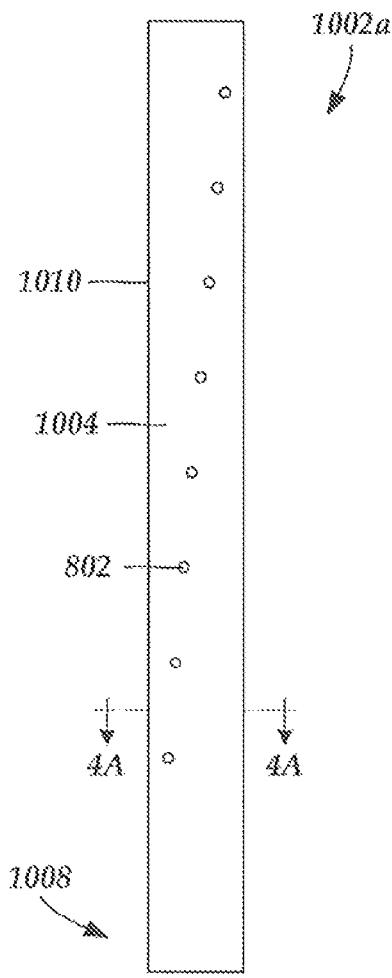
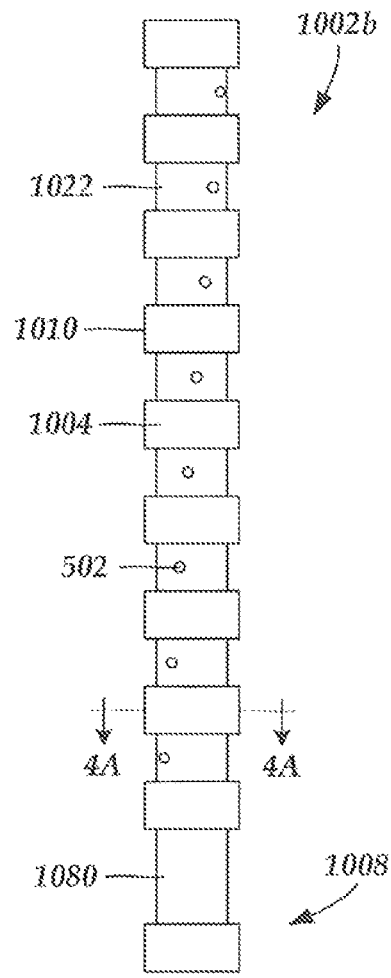
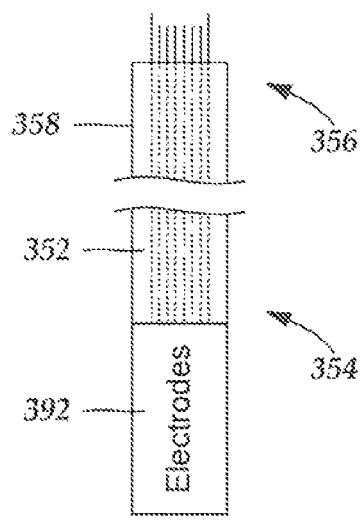
Fig. 10A                    Fig. 10B

SYSTEMS AND METHODS FOR MAKING AND USING CONTACT ASSEMBLIES FOR LEADS OF ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/746, 285 filed Dec. 27, 2012, which is incorporated herein by reference.

FIELD

The present invention is directed to the area of implantable electrical stimulation systems and methods of making and using the systems. The present invention is also directed to implantable electrical stimulation leads having contact assemblies that define conductor lumens each having different lengths, as well as methods of making and using the leads, conductor lumens, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a contact assembly of an electrical stimulation lead includes a contact assembly body formed from an electrically-nonconductive, molded material. The contact assembly body has a first end, a second end, a longitudinal length, a circumference, and an outer side surface. The first end of the contact assembly body is configured and arranged for coupling to an end of a lead body of an electrical stimulation lead. A plurality of side ports is defined along the outer side surface of the contact assembly body. Each side port is longitudinally offset from the remaining side ports along the longitudinal length of the contact assembly. A plurality of conductor lumens is defined along the contact assembly body. Each of the conductor lumens extends from the first end of the contact assembly body and terminates with a different one of the side ports such that each of the conductor lumens has a different length than every other of the conductor lumens. A stylet lumen having a closed end is defined along the contact assembly body. The stylet lumen extends longitudinally from the first end of contact assembly body and terminates at the closed end.

In another embodiment, a method of forming an electrical stimulation lead includes extending a plurality of conductors along a longitudinal length of a lead body with a first end portion of each of the plurality of conductors extending outwards from a first end portion of the lead body. The plurality of conductors includes a first conductor and a second conductor. A molded contact assembly is provided. The contact assembly has a medial end portion and an opposing lateral end portion. The contact assembly defines a plurality of conductor lumens each extending along a portion of a longitudinal length of the contact assembly from the medial end portion of the contact assembly. Each of the plurality of conductor lumens has a different length than every other of the remaining conductor lumens of the plurality of conductor lumens. The plurality of conductor lumens includes a first conductor lumen and a second conductor lumen. The first conductor lumen extends to a first side port defined along an outer side surface of the contact assembly and the second conductor lumen extends to a second side port defined along the outer side surface of the contact assembly. The second side port is longitudinally offset from the first side port along the longitudinal length of the contact assembly. The first end portion of the first conductor is extended into the first conductor lumen from the medial end portion of the contact assembly to the first side port. A first contact is disposed over the first side port. The first end portion of the first conductor is electrically coupled to the first contact. The medial end portion of the contact assembly is coupled to the first end portion of the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 10A is a schematic side view of one embodiment of a contact assembly configured and arranged to couple to a proximal end of the lead body of FIG. 3A, where conductors extend along the lead body and couple to electrodes disposed along a distal end of the lead body, and where the contact assembly is isodiametric, according to the invention;

FIG. 10B is a schematic side view of one embodiment of another embodiment of a contact assembly configured and arranged to couple to a proximal end of the lead body of FIG. 3A, where conductors extend along the lead body and couple to electrodes disposed along a distal end of the lead body, and where the contact assembly defines a plurality of annular grooves formed along an outer side surface of the contact assembly, according to the invention.

DETAILED DESCRIPTION

The present invention is directed to the area of implantable electrical stimulation systems and methods of making and using the systems. The present invention is also directed to implantable electrical stimulation leads having contact assemblies that define conductor lumens each having different lengths, as well as methods of making and using the leads, conductor lumens, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
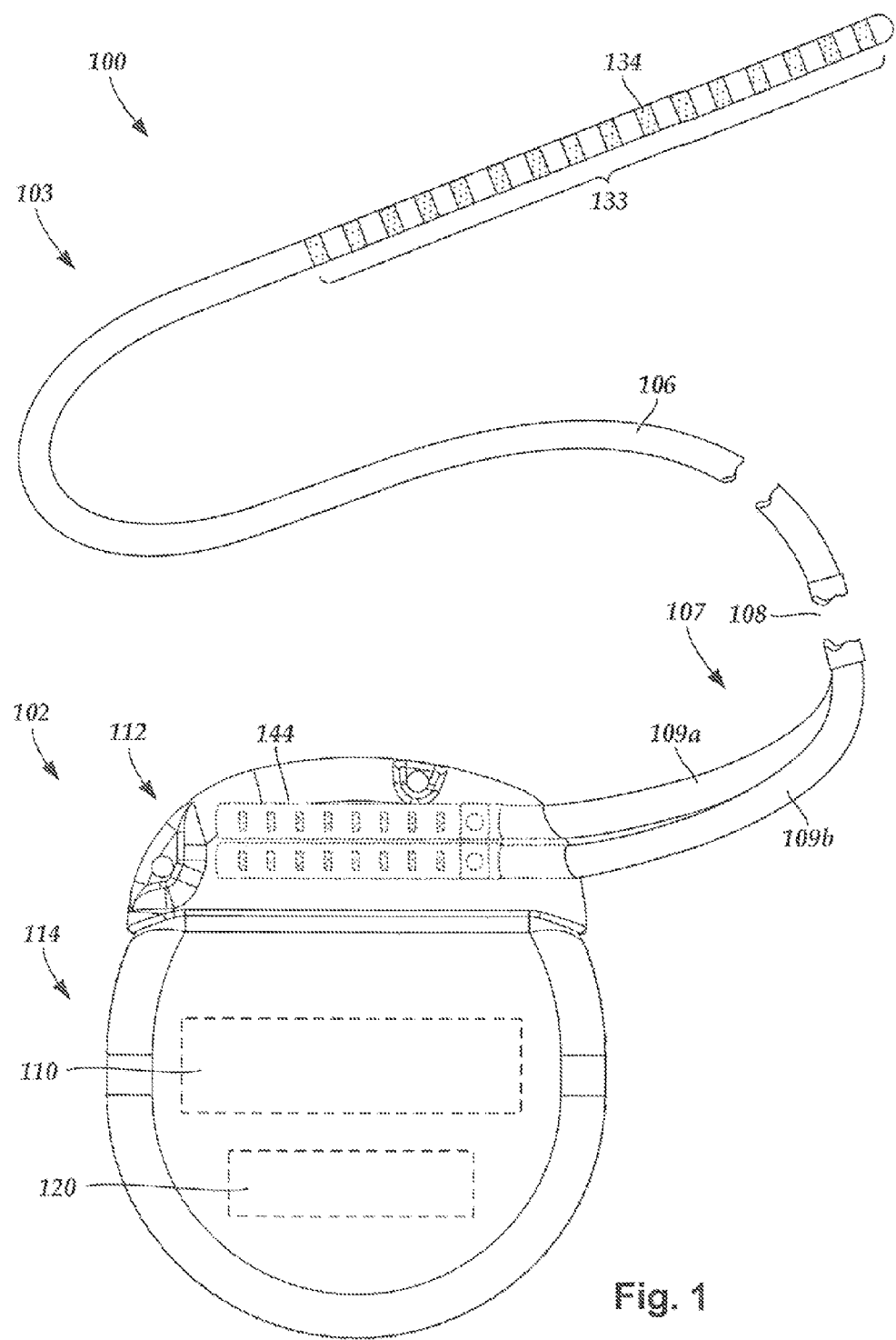
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
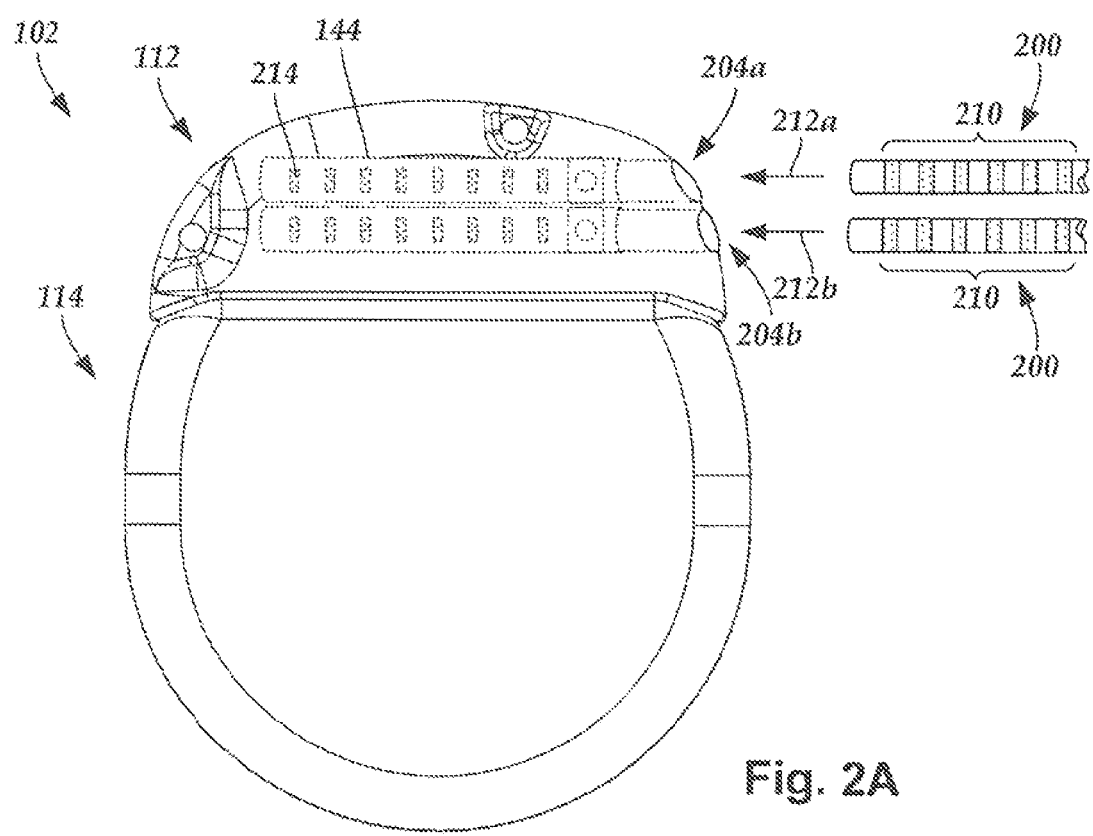
FIG. 2A is a schematic view of one embodiment of the control module of FIG. 1 configured and arranged to electrically couple to an elongated device, according to the invention.
Figure 2B:
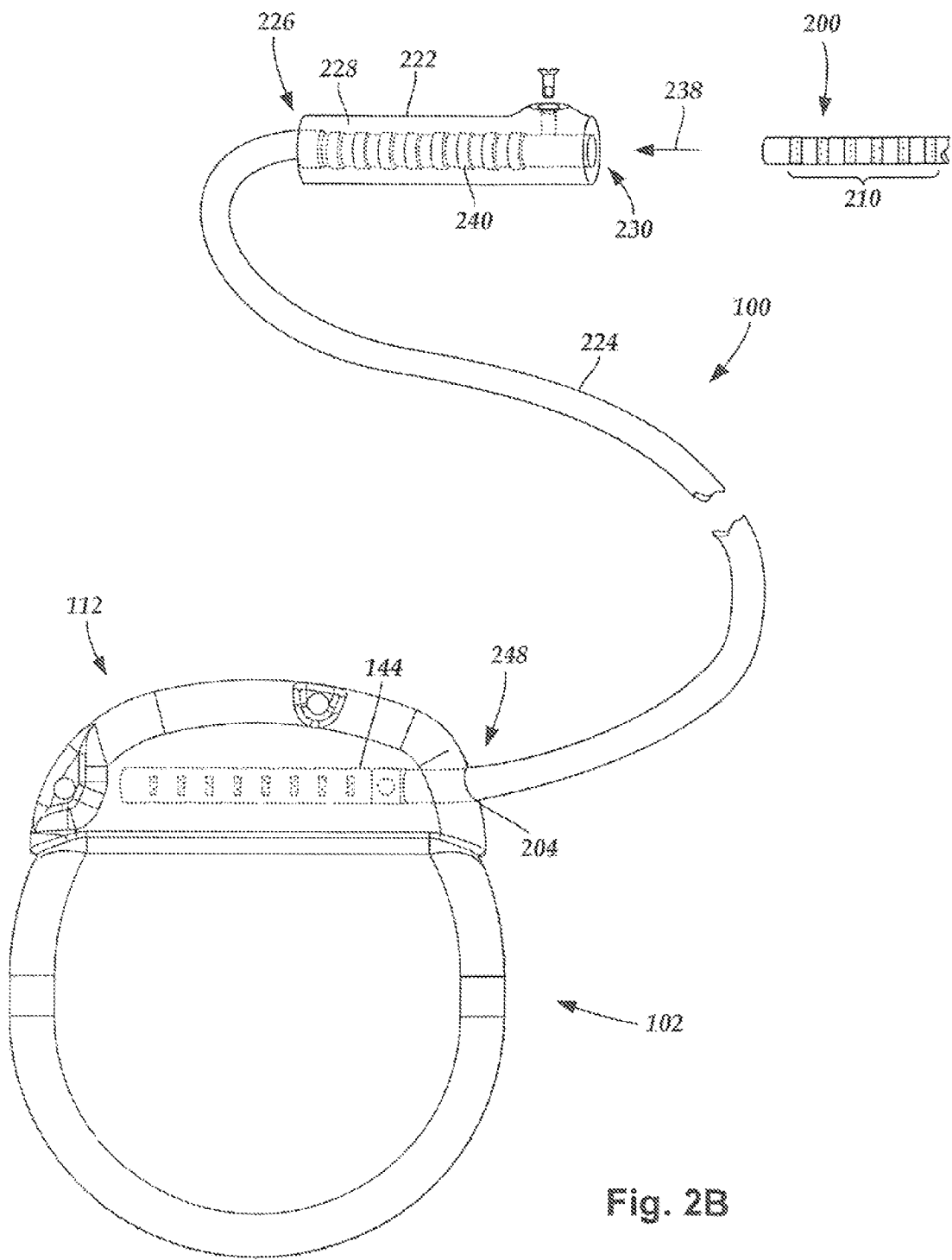
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the lead body 106, for example, for inserting a stylet to facilitate placement of the lead body 106 within a body of a patient. Additionally, there may also be one or more lumens (not shown) that open at, or near, the distal end of the lead body 106, for example, for infusion of drugs or medication into the site of implantation of the one or more lead bodies 106. In at least one embodiment, the one or more lumens may be flushed continually, or on a regular basis, with saline, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Turning to FIG. 3, at least some conventional leads form contact assemblies by ablating end portions of lead bodies and sliding contacts (e.g., terminals and electrodes) onto the ablated end portions of the lead body with electrically-nonconductive spacers disposed between adjacent contacts. Conventional assemblies may also need to be re-flowed and ground down, as well. Forming such contact assemblies may be labor-intensive and provide inconsistent pitches between adjacent contacts. Additionally, forming leads using such techniques may involve inserting one or more monofilaments into end portions of one or more conductor lumens not occupied by conductors (e.g., portions of conductor lumens lateral along the lead from the contacts to which the conductors couple). In which case, the end portions of the leads may need to be re-flowed to melt the monofilaments.

As herein described, contact assemblies for disposing contacts (e.g., electrodes or terminals) along end portions of a lead body are described. In at least some embodiments, the contact assemblies are molded. The contacts disposed along the contact assemblies may be open-loop contacts (i.e., the contacts form a non-continuous loop of material around an open circumference). In which case, the open-loop contacts may be transitioned into closed-loop configurations subsequent to disposing along the contact assembly and prior to implantation. In at least some embodiments, the contacts are disposed along the contact assemblies within annular grooves.

The contact assemblies described herein may eliminate the need to insert monofilaments into conductor lumens. Additionally, the contact assemblies may eliminate the need to ablate the end portions of the lead body to couple the contacts to lead conductors. The contact assemblies described herein may also eliminate re-flowing, or grinding, or both.

Figure 11:
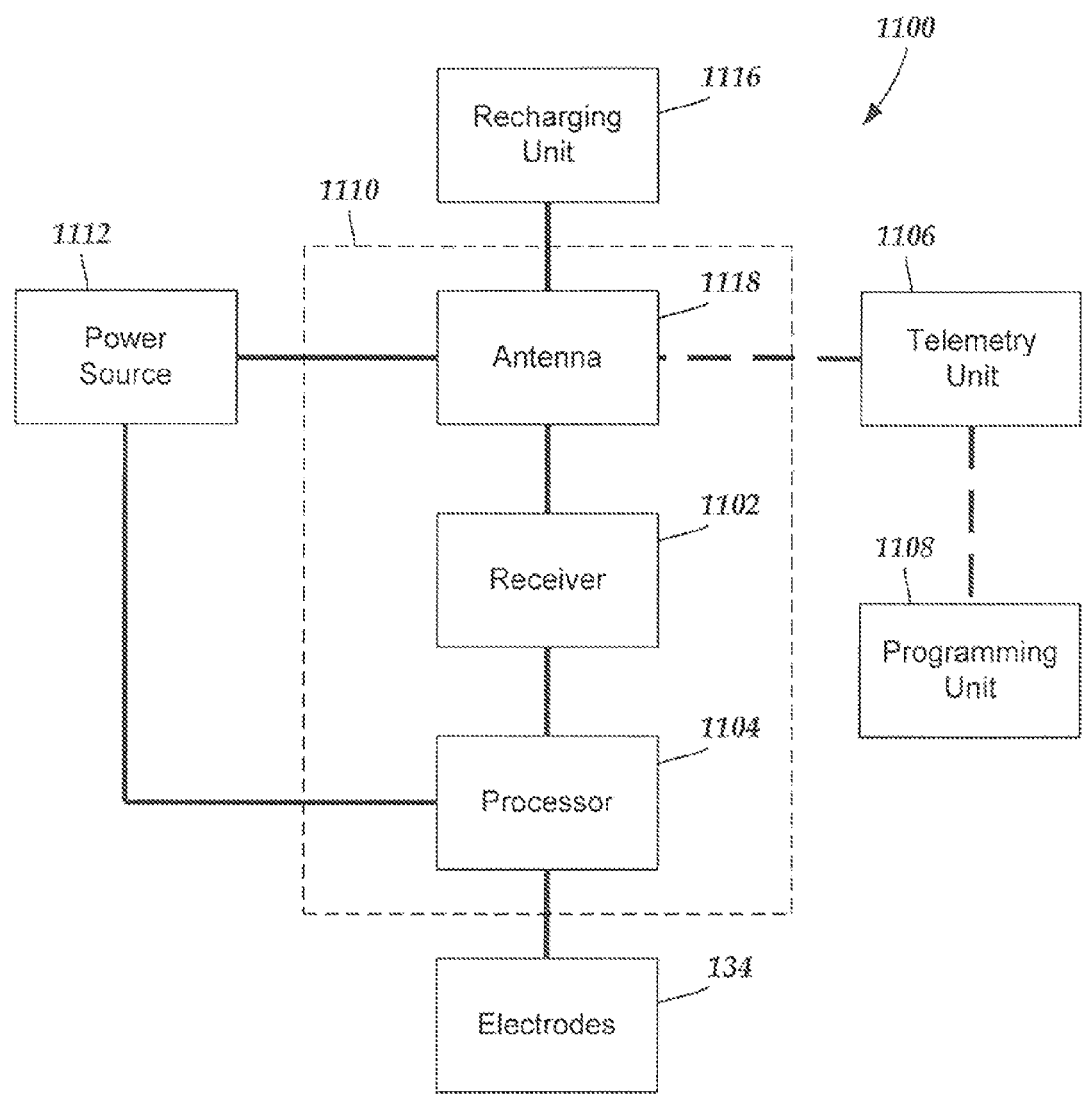
FIG. 11 is a schematic overview of one embodiment of components of a stimulation system, including an electronic subassembly disposed within a control module, according to the invention.

FIGS. 3A-4B illustrate two different contact assemblies configured and arranged for disposing along a distal end of the lead body. FIGS. 5A-9 illustrate two different lead-formation embodiments that involve disposing the contact assemblies of FIGS. 3A-4B along the distal end of a lead body. FIGS. 10-11 illustrate contact assemblies configured and arranged for disposing along a proximal end of the lead body. It will be understood that the lead-formation embodiments of FIGS. 5A-9 apply also to disposing the contact assemblies of FIGS. 10-11 along the proximal end of the lead body in addition to, or in lieu of, disposing the contact assemblies of FIGS. 3A-4B along the distal end of the lead body.

Figure 3A:
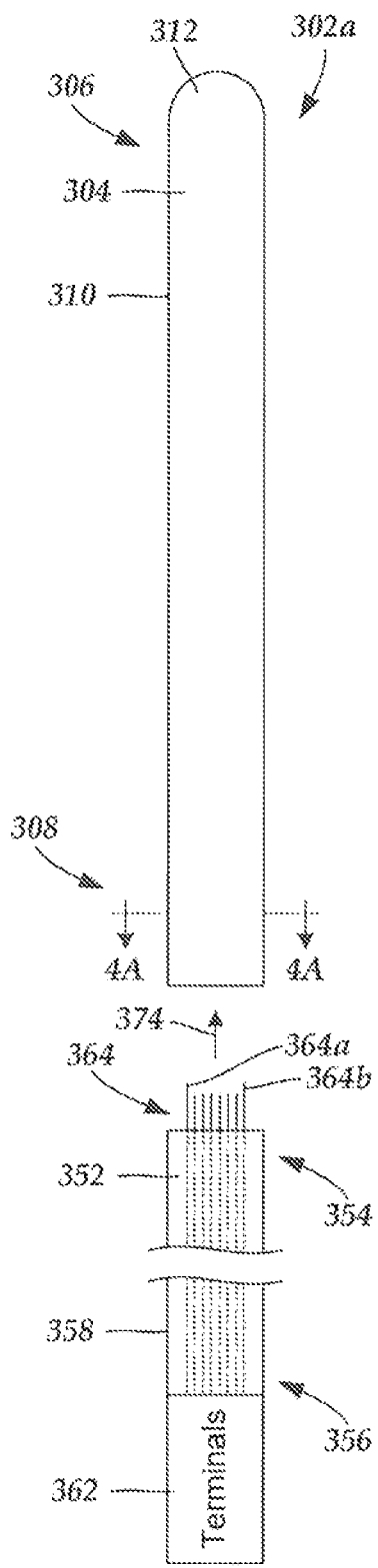
FIG. 3A is a schematic side view of one embodiment of a portion of a lead body and a contact assembly configured and arranged to couple to a distal end of the lead body, where conductors extend along the lead body and couple to terminals disposed along a proximal end of the lead body, and where the contact assembly is isodiametric, according to the invention.
Figure 3B:
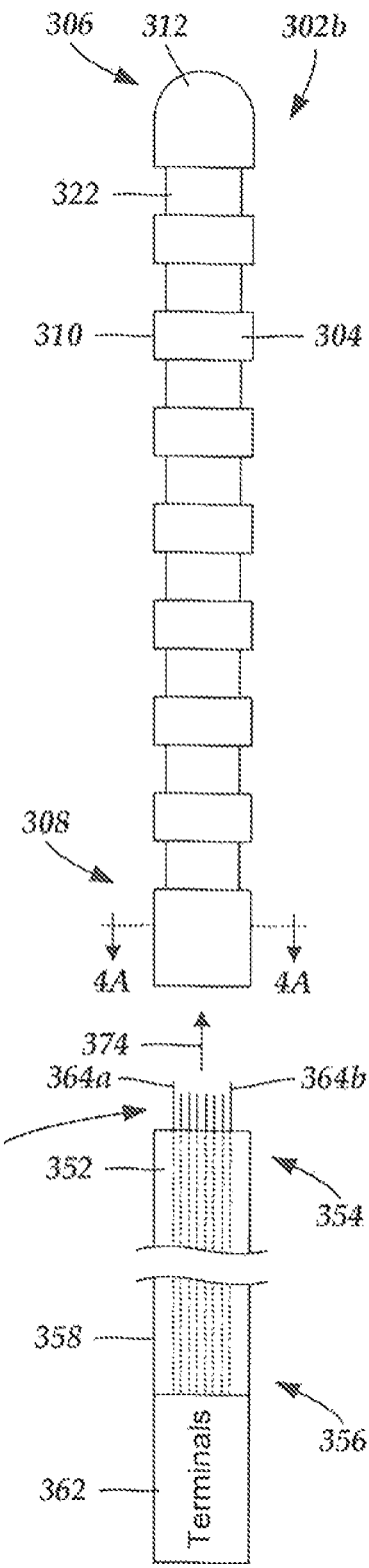
FIG. 3B is a schematic side view of another embodiment of the portion of the lead body of FIG. 3A and a contact assembly configured and arranged to couple to a distal end of the lead body, where conductors extend along the lead body and couple to terminals disposed along a proximal end of the lead body, and where the contact assembly defines a plurality of annular grooves formed along an outer side surface of the contact assembly, according to the invention.

FIGS. 3A and 3B illustrate two different embodiments of contact assemblies suitable for disposing along a distal end portion of a lead body. FIG. 3A shows a contact assembly 302a and FIG. 3B shows a contact assembly 302b. Each of the contact assemblies 302a and 302b include a contact assembly body 304 with a lateral end 306, an opposing medial end 308, and an outer surface 310. The contact assemblies 302a or 302b may, optionally, include a rounded distal tip 312 to facilitate advancement of the lead within a patient.

The rounded distal tip 312 may be formed from any suitable electrically-nonconductive, biocompatible material. In at least some embodiments, the rounded distal tip 312 is formed from one or more materials that are softer than the materials forming other portions of the contact assembly 302a or 302b to reduce the likelihood of causing inadvertent trauma to tissue during implantation or operation. Additionally, for leads that include an inner lumen for stylet insertion (e.g., stylet lumen 404 of FIGS. 4A-4B), the distal tip 312 can form an end stop to prevent an inserted stylet from extending through the lead and potentially piercing patient tissue during lead implantation.

The contact assembly body 304 may have any suitable cross-section including, for example, circular, rectangular, triangular, irregular, oval, or the like. In some embodiments, the contact assembly body 304 is isodiametric along a longitudinal length (as shown in FIG. 3A). Alternately, the contact assembly body 304 may define longitudinally-spaced-apart annular grooves 322 (as shown in FIG. 3B) defined along at least a portion of the longitudinal length of the contact assembly body 304. In at least some embodiments, the annular grooves 322 extend around a complete circumference of the contact assembly 302b.

In FIG. 3B, the annular grooves 322 are shown with a constant spacing between adjacent annular grooves 322. In at least some embodiments, the spacing between adjacent annular grooves 322 may vary. In FIG. 3B, the annular grooves 322 are shown with a constant shape and size. In at least some embodiments, the shape and size of the annular grooves 322 may vary. For example, at least one of the annular grooves 322 may have a different width or depth than at least one other of the annular grooves 322. In FIG. 3B, eight annular grooves 322 are shown. It will be understood that any suitable number of annular grooves 322 can be defined along the outer surface 310 of the contact assembly body 304 including, for example, one, two, three, four, five, six, seven, eight, nine, ten, eleven, twelve, sixteen, twenty, twenty-four, thirty-two, or more annular grooves 322. In at least some embodiments, the number of annular grooves 322 is equal to the number of electrodes disposed on the lead.

FIGS. 3A-3B also show a lead body 352 having a distal end 354, an opposing proximal end 356, and an outer surface 358. The proximal end 356 of the lead body 352 is coupled to terminals 362. The distal end 354 of the lead body 352 is configured and arranged to receive the contact assembly body 304, as shown by directional arrow 374. Conductors 364 are coupled to the terminals 362 and extend along a length of the lead body 352 such that the conductors 364 extend outwardly from the distal end 354 of the lead body 352. The conductors 364 include a first conductor 364a and a second conductor 364b.

In at least some embodiments, the contact assembly body 304 is isodiametric with the lead body 352 prior to being coupled to the lead body 352. In at least some other embodiments, the contact assembly body 304 has a diameter that is either larger, or smaller, than a diameter of the lead body prior to being coupled to the lead body.

Figure 3C:
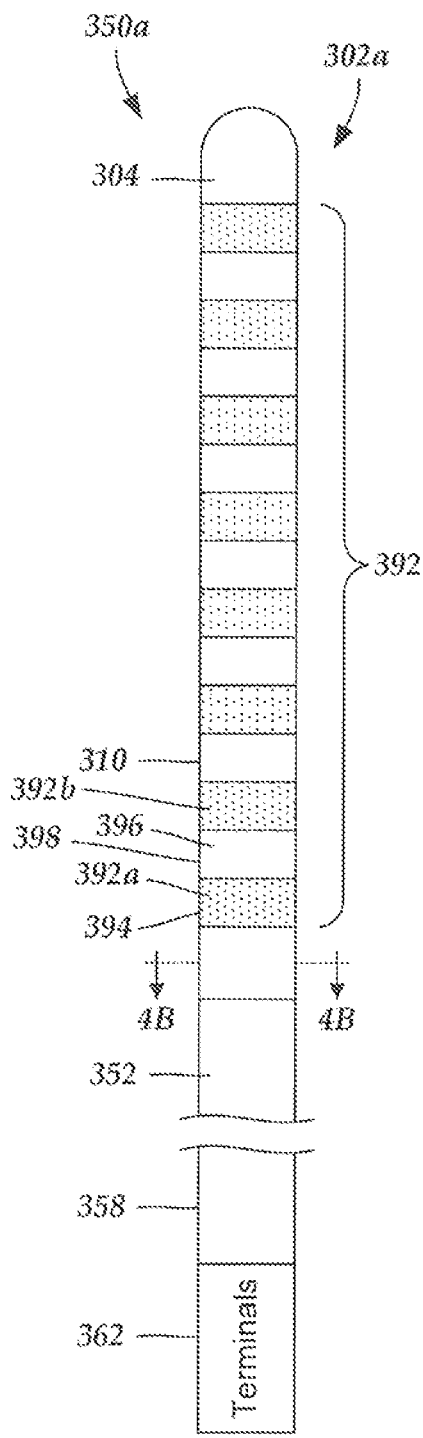
FIG. 3C is a schematic side view of one embodiment of a lead formed using the contact assembly of FIG. 3A and the lead body of FIG. 3A, according to the invention.
Figure 3D:
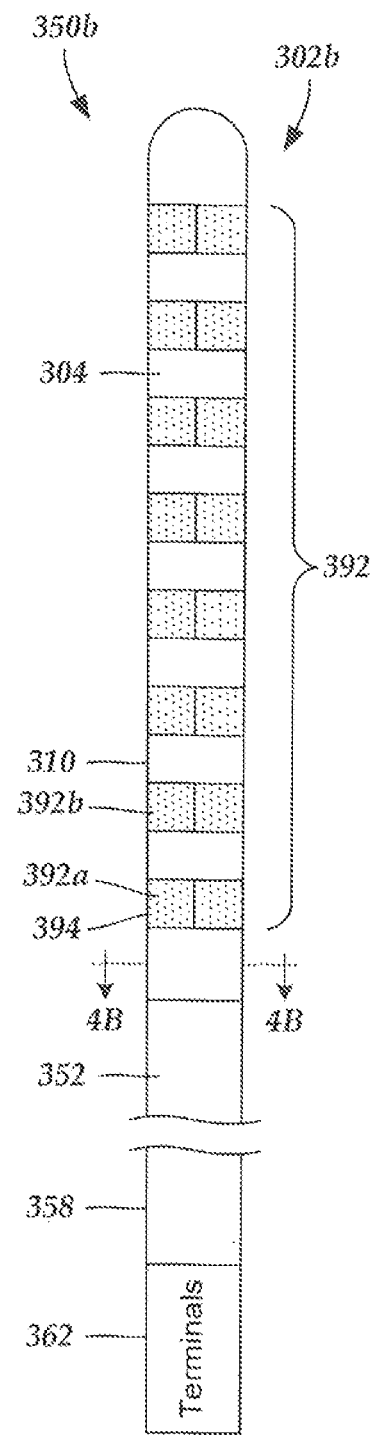
FIG. 3D is a schematic side view of one embodiment of a lead formed using the contact assembly of FIG. 3B and the lead body of FIG. 3B, according to the invention.

FIG. 3C shows the contact assembly 302a coupled to the distal end 354 of the lead body 352 to form a lead 350a. FIG. 3D shows the contact assembly 302b coupled to the distal end 354 of the lead body 352 to form a lead 350b. The contact assemblies 302a and 302b can be coupled to the lead body 352 in any suitable manner including, for example, re-flowing (material of the lead body, the contact assembly, or both), adhesives, or the like.

Electrodes 392 are shown in FIGS. 3C-3D disposed along the contact assembly body 304. The electrodes 392 include a first electrode 392a and a second electrode 392b. The electrodes 394 have outer surfaces 394. In at least some embodiments, the outer surfaces 394 of the electrodes 392 are flush with the outer surface 310 of the contact assembly body 304. In at least some embodiments, the outer surfaces 394 of the electrodes 392 are flush with the outer surface 358 of the lead body 352. In at least some embodiments, the outer surfaces 394 of the electrodes 392 are flush with each of the outer surface 310 of the contact assembly body 304 and the outer surface 358 of the lead body 352.

In at least some embodiments, the electrodes 392 are closed-loop electrodes, where the electrodes form a continuous loop of material around an open circumference. In at least some other embodiments, the electrodes 392 are open-loop electrodes, where the electrodes form a non-continuous loop of material around an open circumference.

In FIG. 3C, the electrodes are shown as being closed-loop electrodes. The electrodes 392 are separated from one another by electrically-nonconductive spacers 396 disposed between adjacent electrodes. The spacers 396 have outer surfaces 398. In at least some embodiments, the outer surfaces 398 of the spacers 396 are flush with the outer surfaces 394 of the electrodes 392. It may be advantageous to use closed-loop electrodes when the contact assembly body 304 is isodiametric. In which case, the electrodes 392 may be slid along the longitudinal length of the contact assembly body 304 into a desired position during formation.

In FIG. 3D, the electrodes are shown as being open-loop electrodes. The open-loop electrodes 392 may include two opposing ends separated from one another by a gap (see e.g., FIG. 6). It may be advantageous to use open-loop electrodes when the contact assembly body 304 defines annular grooves 322 configured to receive the electrodes. In which case, the open-loop electrodes may be configured and arranged to enable the open-loop electrode to slide along the longitudinal length of the contact assembly body 304 while in an open position, then transitioned to a closed position (i.e., the gap between the opposing ends of the electrode is eliminated) when received by a particular annular groove 322. In at least some embodiments, the open-loop electrodes are configured and arranged to enable the open-loop electrode to be disposed directly over the particular annular groove 322 (without sliding the electrodes longitudinally along the contact assembly) and transitioned to a closed position. In at least some embodiments, the open-loop electrodes are configured and arranged to remain in an open position during operation.

In FIG. 3D, the open-loop electrodes are each shown in a closed position and disposed in a different annular groove 322. The portions of the contact assembly body 304 disposed between adjacent annular grooves 322 form electrically-nonconductive spacers between adjacent electrodes 392. In at least some embodiments, a single electrode 392 is disposed in each of the annular grooves 322. The open-loop electrodes 392 may be either permanently or temporarily disposed in the annular grooves 322. Suitable mechanisms for attaching the electrodes to the annular grooves 322 may include re-flowing (material of the contact assembly), one or more adhesives, or the like or combinations thereof.

Figure 4A:
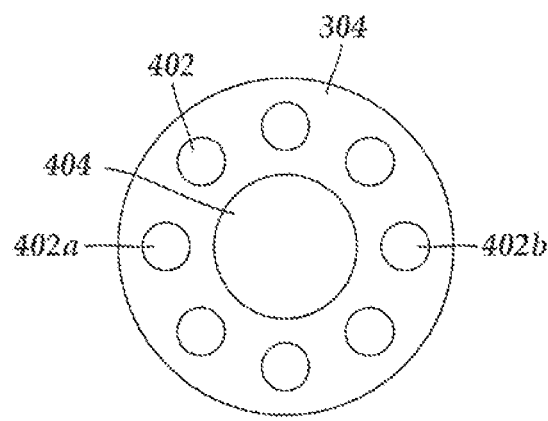
FIG. 4A is a schematic transverse cross-sectional view of one embodiment of the contact assembly of either FIG. 3A or FIG. 3B, the contact assembly defining a plurality of conductor lumens configured for receiving conductors of the lead body of FIGS. 3A and 3B, according to the invention.
Figure 4B:
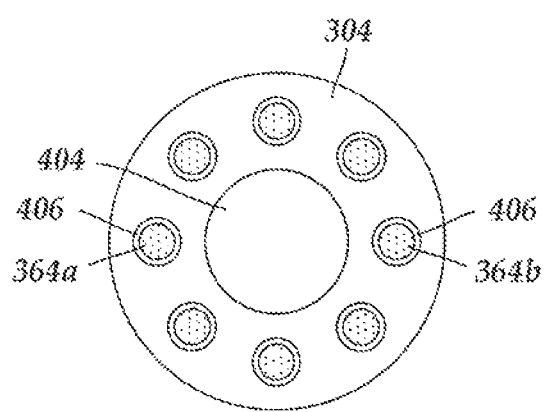
FIG. 4B is a schematic transverse cross-sectional view of one embodiment of the contact assembly of either FIG. 3C or FIG. 3D, with conductors extending along conductor lumens of FIG. 4A defined in the contact assembly, according to the invention.

FIG. 4A illustrates a schematic transverse cross-sectional view of the contact assembly body 304. The contact assembly body 304 defines multiple conductor lumens, such as conductor lumen 402, each configured and arranged to receive one or more of the conductors 364. The conductor lumens include a first conductor lumen 402a and a second conductor lumen 402b. The contact assembly body 304 may, optionally, define a stylet lumen 404 configured and arranged to receive a stylet to facilitate implantation of the lead. As shown in FIG. 4B, in at least some embodiments the first conductor lumen 402a is configured to receive the first conductor 364a of the plurality of conductors, and the second conductor lumen 402b is configured to receive the second conductor 364b of the plurality of conductors.

The conductor lumens may be formed to receive any suitable number of conductors. In FIG. 4A, eight conductor lumens are shown. It will be understood, however, that any number of conductor lumens may be employed. The conductor lumens may be formed to receive any suitable subset of the conductors. In FIG. 4B, a single conductor is shown disposed in each conductor lumen. In at least some embodiments, at least one of the conductor lumens is configured to receive multiple conductors. FIG. 4B shows electrically-nonconductive conductor insulation 406 disposed around the conductors 364 to prevent short-circuiting. This may be especially important in embodiments that include multiple conductors disposed in a given conductor lumen 402.

FIGS. 5A-7 show one embodiment of forming a distal end portion of a lead using the contact assembly 302b. As shown in FIGS. 5A-7, the electrodes 392 are disposed on the contact assembly 302b and electrically coupled to the conductors 364 extending along conductor lumens defined in the contact assembly 302b; the conductors 364 are extended along the lead body 352; and the contact assembly 302b is mechanically coupled to the lead body 352.

In FIGS. 5A-7 (and in other figures), the conductors 364 are shown disposed along the lead body 352 prior to coupling the conductors 364 to the electrodes 392 (or the terminals 372). It will be understood that the conductors 364 may, alternately, be coupled to the electrodes 392 (or the terminals 372) prior to being disposed along the lead body 352.

Figure 5A:
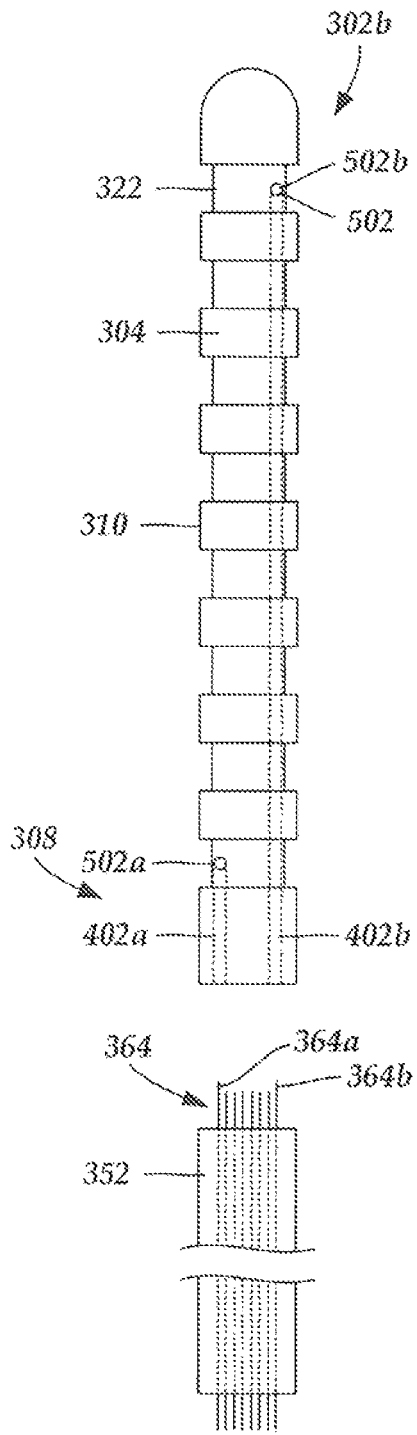
FIG. 5A is a schematic side view of one embodiment of the contact assembly of FIG. 3B illustrating two of the conductor lumens of FIG. 4A extending along the contact assembly from a medial end of the contact assembly to respective side ports defined along an outer side surface of the contact assembly within the annular grooves of FIG. 3B, according to the invention.

FIG. 5A is a schematic side view of the contact assembly 302b and the lead body 352. In FIG. 5A, the conductors 364, including the first conductor 364a and the second conductor 364b, are shown extending along the lead body 352. The contact assembly 302a defines multiple side ports, such as side port 502. The side ports 502 include a first side port 502a and a second side port 502b, defined along the outer surface 310 of the contact assembly 302b. In at least some embodiments, each of the side ports, including the first side port 502a and second side port 502b, is disposed in a different annular groove 322.

The contact assembly 302b defines the first conductor lumen 402a and the second conductor lumen 402b, extending along the contact assembly 302b from the medial end 308 to their respective side ports. As shown in FIG. 5A, the first conductor lumen 402a extends from the medial end 308 of the contact assembly 302b to the first side port 502a, and the second conductor lumen 402b extends from the medial end 308 of the contact assembly 302b to the second side port 502b. In at least some embodiments, the conductor lumens 402 each have a different length from each other. In at least some embodiments, each of the conductor lumens 402 terminates at its respective side port 502.

Figure 5B:
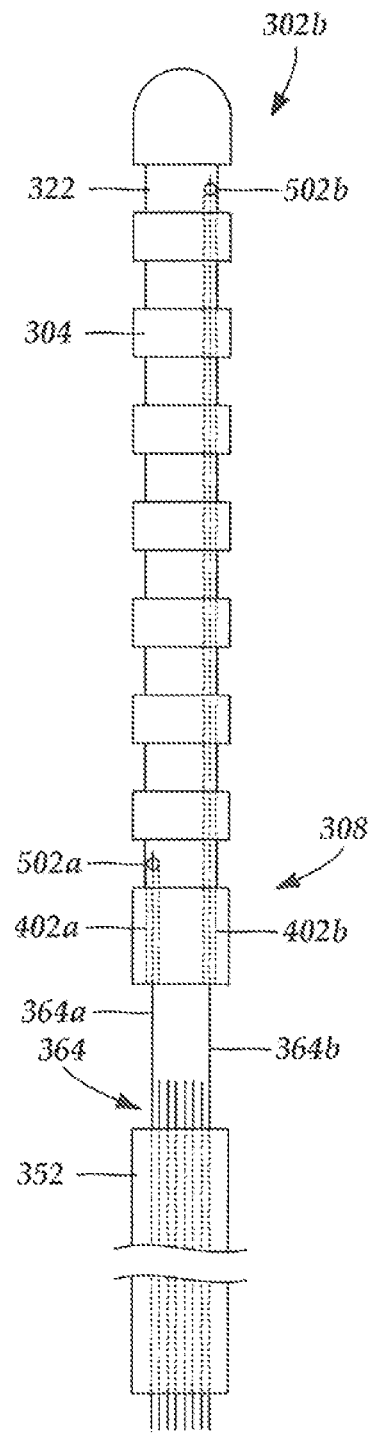
FIG. 5B is a schematic side view of one embodiment of the contact assembly of FIG. 5A illustrating two conductors of the lead body of FIG. 5A extending through the conductor lumens of FIG. 5A to the side ports of FIG. 5A, according to the invention.

Turning to FIG. 5B, the conductors 364 are extended through the conductor lumens 402 of the contact assembly 302b from the medial end 308 of the contact assembly 302b to their respective side ports 502. FIG. 5B shows the first conductor 364a extending along the first conductor lumen 402a from the medial end 308 of the contact assembly 302b to the first side port 502a. Similarly, FIG. 5B shows the second conductor 364b extending along the second conductor lumen 402b from the medial end 308 of the contact assembly 302b to the second side port 502b.

In at least some embodiments, a different side port 502 is disposed in each of the annular grooves 322. In at least some embodiments, each of the side ports 502 opens to a different conductor lumen 402. In at least some embodiments, each of the conductor lumens 402 is configured and arranged to receive a different conductor 364. In at least some embodiments, each of the different conductors 364 is configured and arranged to electrically couple with a different electrode 392 disposed in a different annular groove 322.

Figure 6:
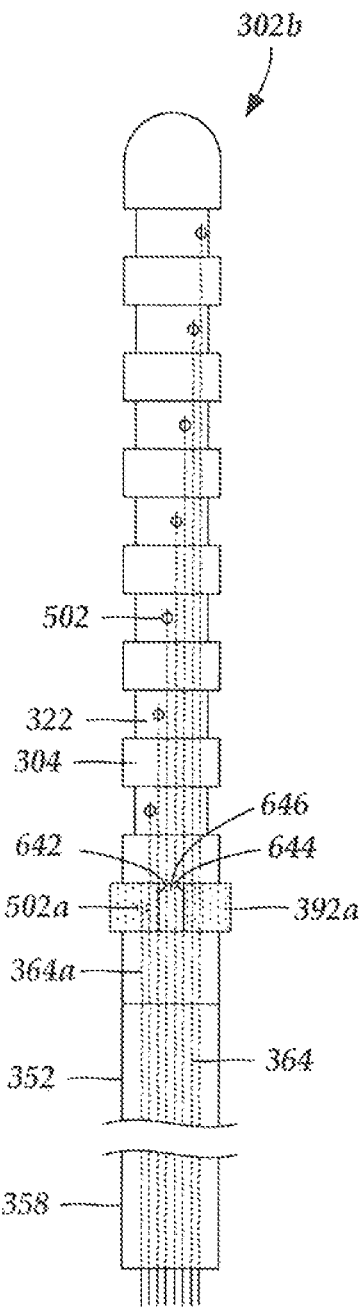
FIG. 6 is a schematic side view of one embodiment of the contact assembly of FIG. 5B abutting one end of the lead body of FIG. 3B, where each conductor of the lead body extends along a different contact lumen of the contact assembly to a different side port, where each side port is defined along a different annular groove formed along the contact assembly, and where an open-loop electrode is disposed in one of the annular grooves and is coupled to the conductor disposed in the side port defined in that annular groove, according to the invention.

Turning to FIG. 6, the electrodes are disposed along the contact assembly 302b. FIG. 6 illustrates a schematic side view of one embodiment of the contact assembly 302b abutting the lead body 352. Conductors 364 each extend along the contact assembly 302b from the medial end 308 of the contact assembly 302b to their respective side ports 502. In FIG. 6 (and in other figures) the conductor lumens 402 of the contact assembly 302b, along which the conductors 364 extend, are omitted for clarity of illustration. In FIG. 6, each of the conductors 364 is shown extending to a different side port 502.

As shown in FIG. 6, the first conductor 364a is extended through the first side port 502a within one of the annular grooves 322. The first electrode 392a is disposed in the annular groove 322 over the first side port 502a and is electrically coupled to the first conductor 364a. In FIG. 6, the first electrode 392a is shown as an open-loop electrode in an open position. As shown in FIG. 6, the first electrode 392a includes a first end 642 and a second end 644 with a gap 646 defined between the first and second ends 642 and 644, respectively.

When the first electrode 392a is an open-loop electrode in the open position (i.e., the gap 646 is formed between the first end 642 and the second end 644), the first electrode 392a may be disposed in the desired annular groove 322 in different ways. For example, the first electrode 392a may be disposed in the desired annular groove 322 by sliding the first electrode 392a along the longitudinal length of the contact assembly 302a from one end of the contact assembly 302a. As another example, the first electrode 392a may be disposed in the desired annular groove 322 by sliding the first electrode 392a directly over the annular groove 322 without sliding the first electrode 392a along a length of the contact assembly 302a.

Figure 7:
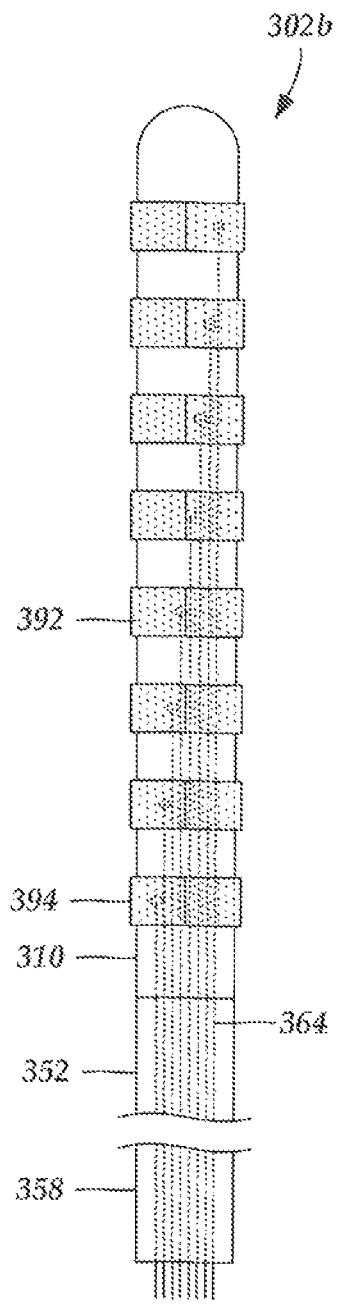
FIG. 7 is a schematic side view of one embodiment of multiple open-loop electrodes disposed over the contact assembly of FIG. 6 and coupled to multiple conductors of the lead body of FIG. 6, where the open-loop electrodes have been transitioned to a closed position, and where the contact assembly is coupled to the lead body, according to the invention.

Turning to FIG. 7, the open-loop electrodes are transitioned to closed positions and electrically coupled to the conductors; and the contact assembly is mechanically coupled to the lead body. FIG. 7 illustrates multiple open-loop electrodes 392 disposed along the contact assembly 302b. The contact assembly 302b is mechanically coupled to the lead body 352. The contact assembly 302b can be mechanically coupled to the lead body 352 in any suitable manner including, for example, re-flowing (material of the lead body, the contact assembly, or both), one or more adhesives, or the like.

In FIG. 7, each of the open-loop electrodes is electrically coupled to a different conductor 364. In at least some embodiments, multiple conductors 364 are electrically coupled to at least one of the electrodes 392. The electrodes 392 may be electrically coupled to the conductors in any suitable manner including, for example, welding, soldering, conductive adhesive, or the like or combinations thereof.

In at least some embodiments, the open-loop electrodes 392 are transitioned to a closed position such that the first ends 642 of the electrodes 392 abut the second ends 644 of the electrodes 392. The open-loop electrodes 392 can be transitioned to a closed position in any suitable manner including, for example, pressing or squeezing together the first ends 642 and the second ends 644 of the electrodes 392. Optionally, once the open-loop electrodes 392 are transitioned to a closed position, the first ends 642 and the second ends 644 of the electrodes 392 may be welded together. In at least some embodiments, the electrodes 392 are mechanically coupled to the contact assembly 302b. The electrodes 392 may be mechanically coupled to the contact assembly 302b in any suitable manner including, for example, re-flowing (material of the contact assembly), one or more adhesives, or the like.

As shown in FIG. 7, in at least some embodiment when the open-loop electrodes 392 are transitioned to a closed position the electrodes 392 have diameters that are larger than a diameter of the contact assembly 302b. In which case, the electrodes 392 may be ground down. In at least some embodiments, the electrodes 392 are ground down until the electrodes 392 are isodiametric with the contact assembly 302b. In at least some embodiments, when the open-loop electrodes 392 are transitioned to a closed position the electrodes 392 have diameters that are equal to a diameter of the contact assembly 302b. In which case, the electrodes 392 may not need to be ground down.

Figure 8:
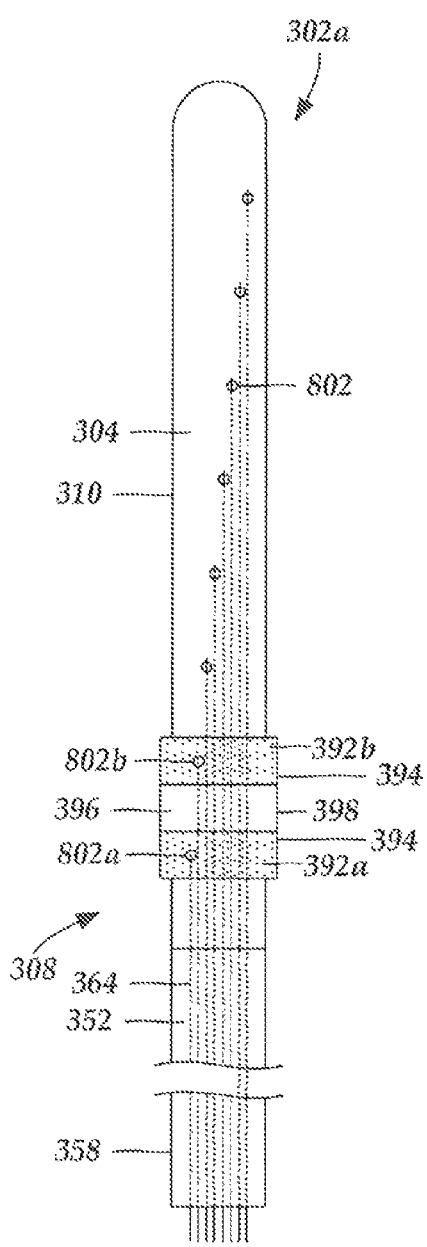
FIG. 8 is a schematic side view of one embodiment of the contact assembly of FIG. 3A abutting one end of the lead body of FIG. 3A, where conductors extend along the lead body and also along the contact assembly to different respective side ports defined along an outer side surface of the contact assembly, where a first closed-loop electrode is disposed over a first side port, where a second closed-loop electrode is disposed over a second side port, and where an electrically-nonconductive spacer is disposed over the outer side surface of the contact assembly between the first electrode and the second electrode, according to the invention.
Figure 9:
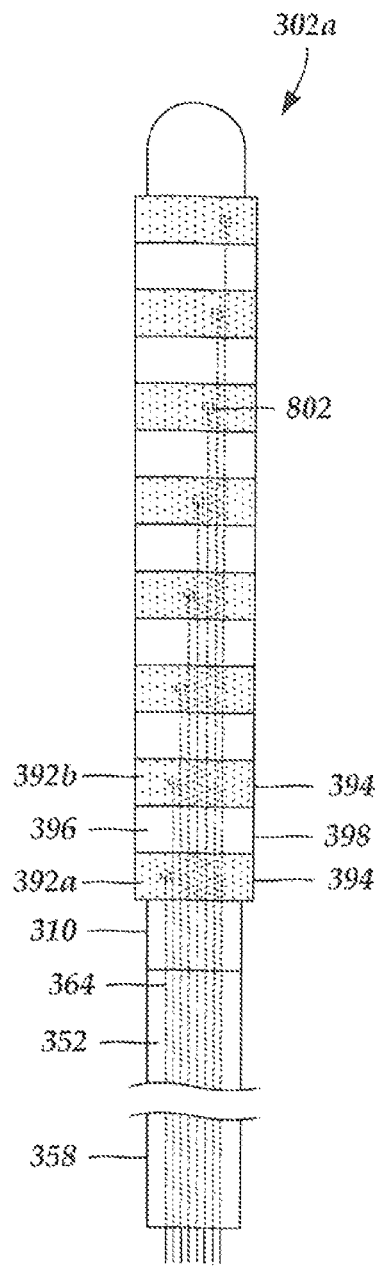
FIG. 9 is a schematic side view of one embodiment of the contact assembly of FIG. 8, where multiple closed-loop electrodes are disposed over the side ports of FIG. 8 and are coupled to the conductors of FIG. 8 extending through the side ports, where electrically-nonconductive spacers are disposed between adjacent electrodes, and where the contact assembly is coupled to the lead body of FIG. 3B, according to the invention.

FIGS. 8-9 show one embodiment of forming a distal end portion of a lead using the contact assembly 302a. As shown in FIGS. 8-9, the electrodes 392 are disposed on the contact assembly 302a and electrically coupled to the conductors 364 extending along conductor lumens defined in the contact assembly 302a; the conductors 364 are extended along the lead body 352; and the contact assembly 302a is mechanically coupled to the lead body 352.

FIG. 8 is a schematic side view of the contact assembly 302a abutting one end of the lead body 352. The contact assembly body 304 defines multiple side ports 802, including a first side port 802a and a second side port 802b. Each of the side ports 802 are coupled to the conductor lumens 402, as described above with reference to FIGS. 5A-5B. In at least some embodiments, the conductor lumens 402 each have a different length from each other. In at least some embodiments, each of the conductor lumens 402 terminates at its respective side port 502. In at least some embodiments, the contact assembly 302a is isodiametric with the lead body 352. In at least some other embodiments, the contact assembly 302a has a diameter that is smaller than a diameter of the lead body 352.

In at least some embodiments, multiple conductors 364 extend along the contact assembly 302a. In FIG. 8, the conductors 364 are each shown extending along the contact assembly 302a from the medial end 308 of the contact assembly 302a to their respective side port 802. In at least some embodiments, the side ports 802 are defined along the outer surface 310 of the contact assembly 302a such that the side ports 802 are longitudinally-spaced-apart from one another along a longitudinal length of the contact assembly 302a. The side ports 802 are defined along the outer surface 310 of the contact assembly 302a and are in communication with the conductor lumens 402. The conductor lumens 402 are omitted in FIG. 8, for clarity of illustration. In FIG. 8, each of the conductors 364 is shown extending from a different side port 802.

In FIG. 8, the first electrode 392a is shown disposed over the first side port 802a and is electrically coupled to the conductor 364 extending from the first side port 802a. Additionally, FIG. 8 shows the second electrode 392a disposed over the second side port 802b and electrically coupled to the conductor 364 extending from the second side port 802b. In at least some embodiments, the spacer 396 is disposed between the first electrode 392a and the second electrode 392b.

FIG. 9 shows a different electrode 392 disposed over each of the remaining side ports 802, with spacers 396 disposed between adjacent electrodes 392. The contact assembly 302a is mechanically coupled to the lead body 352. In at least some embodiments, the electrodes 392 are closed-loop. In which case, in at least some embodiments the electrodes 392 are slid longitudinally along the contact assembly 302a over the outer surface 310 of the contact assembly 302a.

The electrodes 392 are electrically coupled to the conductors 364. In at least some embodiments, the electrodes 392 are mechanically coupled (e.g., re-flowing material of the contact assembly, or the spacers 396, or both; applying one or more adhesives, or the like or combinations thereof) to the outer surface 310 of the contact assembly 302a. In at least some embodiments, the electrodes 392 and the spacers 396 have diameters that are larger than a diameter of the lead body 352. In which case, the electrodes 392 and the spacers 396 may be ground down. In at least some embodiments, the electrodes 392 and the spacers 396 are ground down to be isodiametric with the lead body 352. In at least some embodiments, when, for example, the contact assembly 302a has a diameter that is smaller than a diameter of the lead body 352, the electrodes 392 and the spacers 396 may be isodiametric with the lead body 352 without grinding down the electrodes 392 and spacers 396.

Turning to FIGS. 10A-10B, a contact assembly may be disposed along the proximal end portion of the lead in lieu of, or in addition to, disposing a contact assembly along the distal end portion of the lead. It will be understood that connector assemblies disposed along the proximal end portion of the lead may include the same features (e.g., conductor lumens of different lengths extending between a medial end of the contact assembly and side ports longitudinally spaced apart from one another along a length of the contact assembly) as described above with respect to the contact assemblies 302a and 302b, including the same mechanical coupling of the contacts to the contact assembly, and the contact assembly to the lead body, as well as the same electrical coupling between the contacts disposed on the contact assembly and the conductors.

FIG. 10A is a schematic side view of one embodiment of a contact assembly 1002a configured and arranged for disposing along the proximal end portion 356 of the lead body 352. FIG. 10B is a schematic side view of another embodiment of a contact assembly 1002b configured and arranged for disposing along the proximal end portion 356 of the lead body 352.

The contact assemblies 1002a and 1002b each include a contact assembly body 1004 having an outer surface 1010 and a medial end 1080. Side ports (502 in FIGS. 10A and 802 in FIG. 10B) are defined along the outer surface 1010 of the contact assembly body 1004 and are coupled to conductor lumens 402 (not shown in FIGS. 10A-10B) that each extend between a different side port and the medial end 1080 of the contact assembly body 1004.

In FIG. 10A, the contact assembly body 1004 is isodiametric. In FIG. 10B, the contact assembly body 1004 defines multiple longitudinally-spaced-apart annular grooves 1022 configured and arranged for receiving terminals (see e.g., terminals 362 of FIG. 3D). Optionally, the contact assembly body 1004 of the contact assembly 1002b may define an annular groove 1080 configured and arranged to receive a retention sleeve for facilitating coupling of the contact assembly 1002b to a connector (see e.g., connector 144 of FIG. 1; and connector 22 of FIG. 2B).

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A contact assembly of an electrical stimulation lead, the contact assembly comprising:
    a cylindrical contact assembly body formed from an electrically-nonconductive, molded material, the contact assembly body having a first end, a second end, a longitudinal length, a circumference, and an outer side surface, wherein the first end of the contact assembly body is configured and arranged for coupling to an end of a lead body of an electrical stimulation lead;
    a plurality of side ports defined along the outer side surface of the contact assembly body, wherein each side port of the plurality of side ports is longitudinally and circumferentially offset from the remaining side ports of the plurality of side ports along the longitudinal length of the contact assembly;
    a plurality of conductor lumens defined along the contact assembly body, wherein each of the conductor lumens extends from the first end of the contact assembly body and terminates with a different one of the side ports of the plurality of side ports such that each of the plurality of conductor lumens has a different length than every other of the conductor lumens; and
    a stylet lumen defined along the contact assembly body, the stylet lumen having a closed end, wherein the stylet lumen extends longitudinally from the first end of contact assembly body and terminates at the closed end.

2. The contact assembly of claim 1, further comprising a plurality of longitudinally-spaced-apart annular grooves formed along the outer side surface of the contact assembly body, each annular groove of the plurality of annular grooves extending entirely around the circumference of the contact assembly body.

3. The contact assembly of claim 2, wherein each of the side ports is defined in a different one of the plurality of annular grooves.

4. An electrical stimulation lead, comprising:
    the contact assembly of claim 1;
    a lead body having a distal end portion, a proximal end portion, and a longitudinal length, wherein the first end of the contact assembly is coupled to the distal end portion of the lead body;
    a plurality of longitudinally-spaced-apart electrodes disposed over the contact assembly body, wherein each of the plurality of electrodes is disposed over a different side port of the plurality of side ports of the contact assembly;
    a plurality of terminals coupled to the proximal end portion of the lead body; and
    a plurality of conductors electrically coupling the plurality of terminals to the plurality of electrodes.

5. An electrical stimulation lead, comprising:
    a contact assembly comprising
        a contact assembly body formed from an electrically-nonconductive, molded material, the contact assembly body having a first end, a second end, a longitudinal length, a circumference, and an outer side surface, wherein the first end of the contact assembly body is configured and arranged for coupling to an end of a lead body of an electrical stimulation lead,
        a plurality of side ports defined along the outer side surface of the contact assembly body, wherein each side port of the plurality of side ports is longitudinally offset from the remaining side ports of the plurality of side ports along the longitudinal length of the contact assembly,
        a plurality of conductor lumens defined along the contact assembly body, wherein each of the conductor lumens extends from the first end of the contact assembly body and terminates with a different one of the side ports of the plurality of side ports such that each of the plurality of conductor lumens has a different length than every other of the conductor lumens, and
        a stylet lumen defined along the contact assembly body, the stylet lumen having a closed end, wherein the stylet lumen extends longitudinally from the first end of contact assembly body and terminates at the closed end; and
    a lead body having a distal end portion, a proximal end portion, and a longitudinal length, wherein the first end of the contact assembly is coupled to the distal end portion of the lead body;
    a plurality of longitudinally-spaced-apart electrodes disposed over the contact assembly body, wherein each of the plurality of electrodes is disposed over a different side port of the plurality of side ports of the contact assembly;
    a plurality of terminals coupled to the proximal end portion of the lead body; and
    a plurality of conductors electrically coupling the plurality of terminals to the plurality of electrodes; and
    a plurality of longitudinally-spaced-apart non-conductive spacers disposed over the contact assembly, and wherein each of the plurality of spacers is flanked by two adjacent electrodes of the plurality of electrodes.

6. The electrical stimulation lead of claim 4, wherein the contact assembly body defines a plurality of longitudinally-spaced-apart annular grooves formed along the outer side surface of the contact assembly body, and wherein each electrode of the plurality of electrodes is disposed in a different annular groove of the plurality of annular grooves.

7. The electrical stimulation lead of claim 4, wherein the electrical stimulation lead is isodiametric.

8. The electrical stimulation lead of claim 4, wherein the contact assembly is a first contact assembly, and further comprising a second contact assembly coupled to the proximal end portion of the lead body, wherein the plurality of terminals are disposed over the second contact assembly.

9. An electrical stimulating system comprising:
the electrical stimulation lead of claim 4;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end portion of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals of the electrical stimulation lead.

10. An electrical stimulation lead, comprising:
the contact assembly of claim 1;
a lead body having a distal end portion, a proximal end portion, and a longitudinal length, wherein the first end of the contact assembly is coupled to the proximal end portion of the lead body;
a plurality of longitudinally-spaced-apart terminals disposed over the contact assembly body, wherein each of the plurality of terminals is disposed over a different side port of the plurality of side ports of the contact assembly;
a plurality of electrodes coupled to the distal end portion of the lead body; and
a plurality of conductors electrically coupling the plurality of terminals to the plurality of electrodes.

11. An electrical stimulation lead, comprising:
a contact assembly comprising
a contact assembly body formed from an electrically-nonconductive, molded material, the contact assembly body having a first end, a second end, a longitudinal length, a circumference, and an outer side surface, wherein the first end of the contact assembly body is configured and arranged for coupling to an end of a lead body of an electrical stimulation lead,
a plurality of side ports defined along the outer side surface of the contact assembly body, wherein each side port of the plurality of side ports is longitudinally offset from the remaining side ports of the plurality of side ports along the longitudinal length of the contact assembly,
a plurality of conductor lumens defined along the contact assembly body, wherein each of the conductor lumens extends from the first end of the contact assembly body and terminates with a different one of the side ports of the plurality of side ports such that each of the plurality of conductor lumens has a different length than every other of the conductor lumens, and
a stylet lumen defined along the contact assembly body, the stylet lumen having a closed end, wherein the stylet lumen extends longitudinally from the first end of contact assembly body and terminates at the closed end:
a lead body having a distal end portion, a proximal end portion, and a longitudinal length, wherein the first end of the contact assembly is coupled to the distal end portion of the lead body;
a plurality of longitudinally-spaced-apart terminals disposed over the contact assembly body, wherein each of the plurality of terminals is disposed over a different side port of the plurality of side ports of the contact assembly;
a plurality of electrodes coupled to the distal end portion of the lead body;
a plurality of conductors electrically coupling the plurality of terminals to the plurality of electrodes; and
a plurality of longitudinally-spaced-apart non-conductive spacers disposed over the contact assembly, wherein each of the plurality of spacers is flanked by two adjacent terminals of the plurality of terminals.

12. The electrical stimulation lead of claim 10, wherein the contact assembly body defines a plurality of longitudinally-spaced-apart annular grooves formed along the outer side surface of the contact assembly body, and wherein each terminal of the plurality of terminals is disposed in a different annular groove of the plurality of annular grooves.

13. A method of forming an electrical stimulation lead using the contact assembly of claim 1, the method comprising:
extending a plurality of conductors along a longitudinal length of a lead body with a first end portion of each of the plurality of conductors extending outwards from a first end portion of the lead body, wherein the plurality of conductors comprises a first conductor and a second conductor;
providing the contact assembly, wherein the plurality of conductor lumens comprises a first conductor lumen and a second conductor lumen, the first conductor lumen extending to a first side port defined along an outer side surface of the contact assembly and the second conductor lumen extending to a second side port defined along the outer side surface of the contact assembly, wherein the second side port is longitudinally offset from the first side port along the longitudinal length of the contact assembly;
extending the first end portion of the first conductor into the first conductor lumen from the first end of the contact assembly to the first side port;
disposing a first contact over the first side port;
electrically coupling the first end portion of the first conductor to the first contact; and
coupling the first end of the contact assembly to the first end portion of the lead body.

14. The method of claim 13, wherein disposing a first contact over the first side port comprises disposing a first open-loop contact within a first annular groove defined in the outer side surface of the contact assembly.

15. The method of claim 13, wherein disposing a first contact over the first side port comprises disposing a first closed-loop contact over the first side port.

16. The method of claim 13, wherein coupling the first end of the contact assembly to the first end portion of the lead body comprises re-flowing at least one of material of the contact assembly or material of the lead body.

17. The method of claim 13, further comprising re-flowing material of the contact assembly, after electrically coupling the first end portion of the first conductor to the first contact, to facilitate attachment of the first contact to the contact assembly.

18. The method of claim 13, further comprising grinding the first contact, after electrically coupling the first end portion of the first conductor to the first contact, to make the electrical stimulation lead isodiametric.

19. The method of claim 13, further comprising
extending the first end portion of the second conductor into the second conductor lumen from the first end of the contact assembly to the second side port;
disposing a second contact over the second side port; and
electrically coupling the first end portion of the second conductor to the second contact.

20. The method of claim 19, further comprising disposing an electrically non-conductive spacer over a portion of the contact assembly between the first side port and the second side port prior to disposing the second contact over the second side port.

* * * * *